US00PP31808P3

(12) United States Plant Patent
Suphachadiwong

(10) Patent No.: US PP31,808 P3
(45) Date of Patent: May 26, 2020

(54) *VANDA* PLANT NAMED 'SPCDW1809'

(50) Latin Name: *Vanda* spp. Jones ex R. Br.
Varietal Denomination: SPCDW1809

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 16/501,499

(22) Filed: Apr. 18, 2019

(65) Prior Publication Data

US 2019/0327874 P1 Oct. 24, 2019

(30) Foreign Application Priority Data

Apr. 18, 2018 (QZ) ..... PBR 2018/1078

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
None
See application file for complete search history.

*Primary Examiner* — Susan McCormick Ewoldt
(74) *Attorney, Agent, or Firm* — Samuel R. McCoy, Jr.

(57) ABSTRACT

A new and distinct *Vanda* plant named 'SPCDW1809' which is characterized by a freely flowering bloom habit, with an abundance of large coral-colored flowers carried within or slightly above the foliage, a dorsal sepal and lateral petals which are moderately dotted greyed-purple, lateral sepals which are heavily dotted and blotched greyed-purple, a labellum with a dark greyed-purple central lobe and yellow-green lateral lobes which are radially striped with greyed-orange, and the stability of these characteristics from generation to generation.

4 Drawing Sheets

CROSS REFERENCE TO RELATED APPLICATIONS

This application claims priority to the Community Plant Variety Rights application number 2018/1078, filed Apr. 18, 2018, which is herein incorporated by reference.

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1809'.

BACKGROUND OF THE INVENTION

Parentage: The new *Vanda* plant, 'SPCDW1809', is the result of a planned breeding program. 'SPCDW1809' originated as a seedling from the controlled pollination of *Vanda* 'GM' (not patented), the seed parent, with *Vanda* 'M81R1' (not patented), the pollen parent. Both parents were developed by, and are owned by, the inventor and were never commercially released. The crossing was made by the inventor in his research greenhouse in Bangphra, Thailand in October of 1996.

The new variety was first selected in March of 2001, in a research greenhouse in Bangphra, Thailand belonging to the inventor. After identifying the new variety as a potentially interesting selection, the inventor continued confidential testing and propagation of 'SPCDW1809', assessing stability of the unique characteristics of this variety.

Asexual Reproduction: Asexual reproduction of the new cultivar 'SPCDW1809', by way of mericloning, was first initiated in September of 2011 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1809' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1809'. These characteristics in combination distinguish 'SPCDW1809' as a new and distinct *Vanda* cultivar:

1. *Vanda* 'SPCDW1809' exhibits a freely flowering bloom habit, with an abundance of large flowers carried within or slightly above the foliage; and
2. *Vanda* 'SPCDW1809' exhibits a light yellow dorsal sepal and light yellow lateral petals, all of which are lightly suffused with greyed-red, creating a coral coloration; and
3. *Vanda* 'SPCDW1809' exhibits a dorsal sepal and lateral petals which are moderately dotted greyed-purple; and
4. *Vanda* 'SPCDW1809' exhibits light yellow lateral sepals which are suffused with greyed-purple at and towards the margins; and 5. *Vanda* 'SPCDW1809' exhibits lateral sepals heavily dotted and blotched greyed-purple; and
6. *Vanda* 'SPCDW1809' exhibits a labellum with a greyed-red central lobe that becomes progressively suffused with greyed-purple towards the apex, and yellow-green lateral lobes which are radially striped with greyed-orange.

BOTANICAL DESCRIPTION OF THE PLANT

Figure 1:
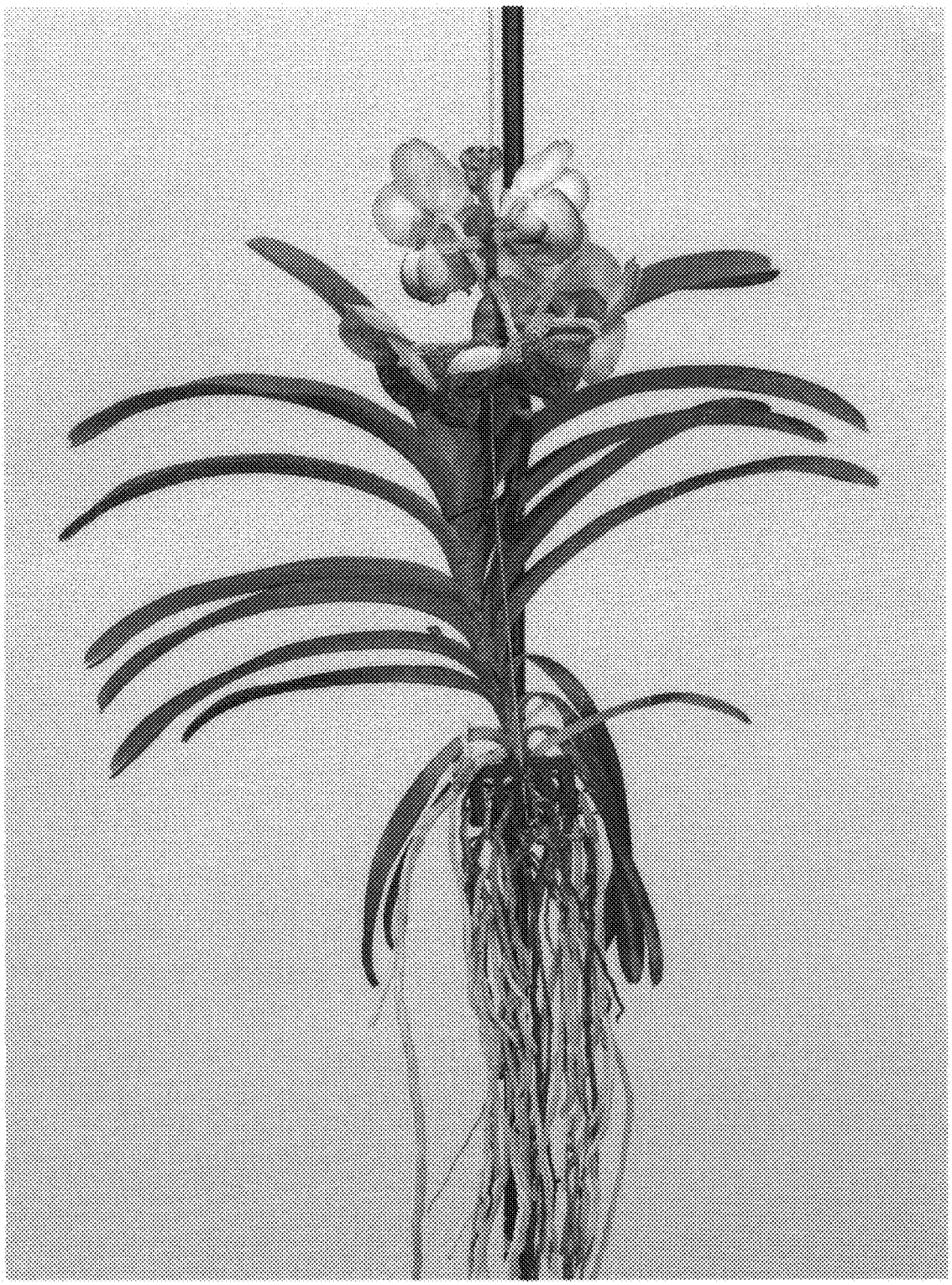
FIG. 1 illustrates, as nearly true as it is reasonably possible to make the same in color photographs of this type, an exemplary plant of 'SPCDW1809' grown in a commercial greenhouse in Honselersdijk, the Netherlands. This plant is approximately 6 years old from the time of mericloning, shown planted in an 8 by 2 cm container.
Figure 2:
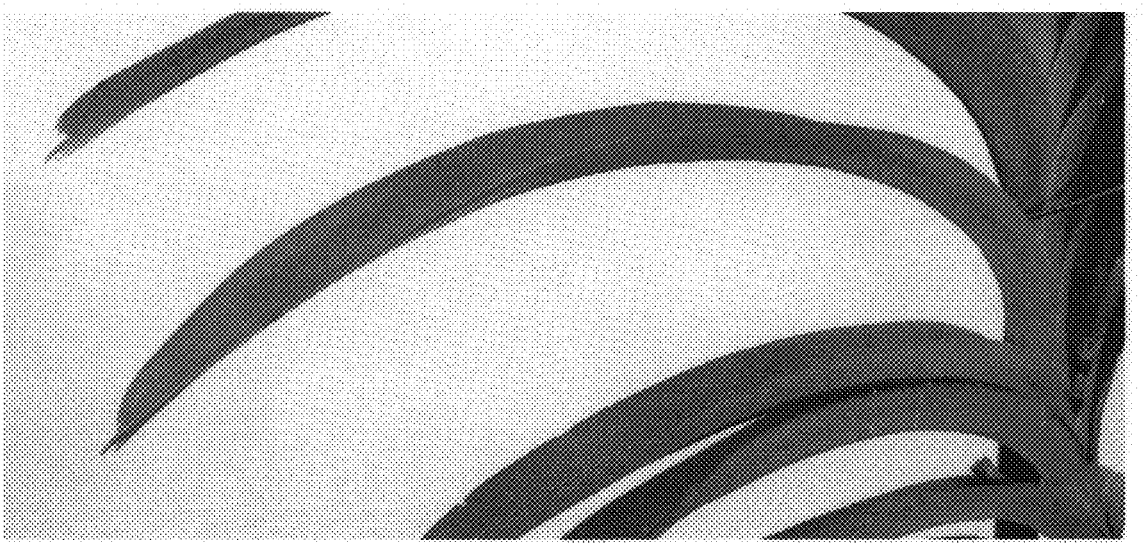
FIG. 2 illustrates, as nearly true as it is reasonably possible to make the same in color photographs of this type, the typical foliage of 'SPCDW1809'.
Figure 3:
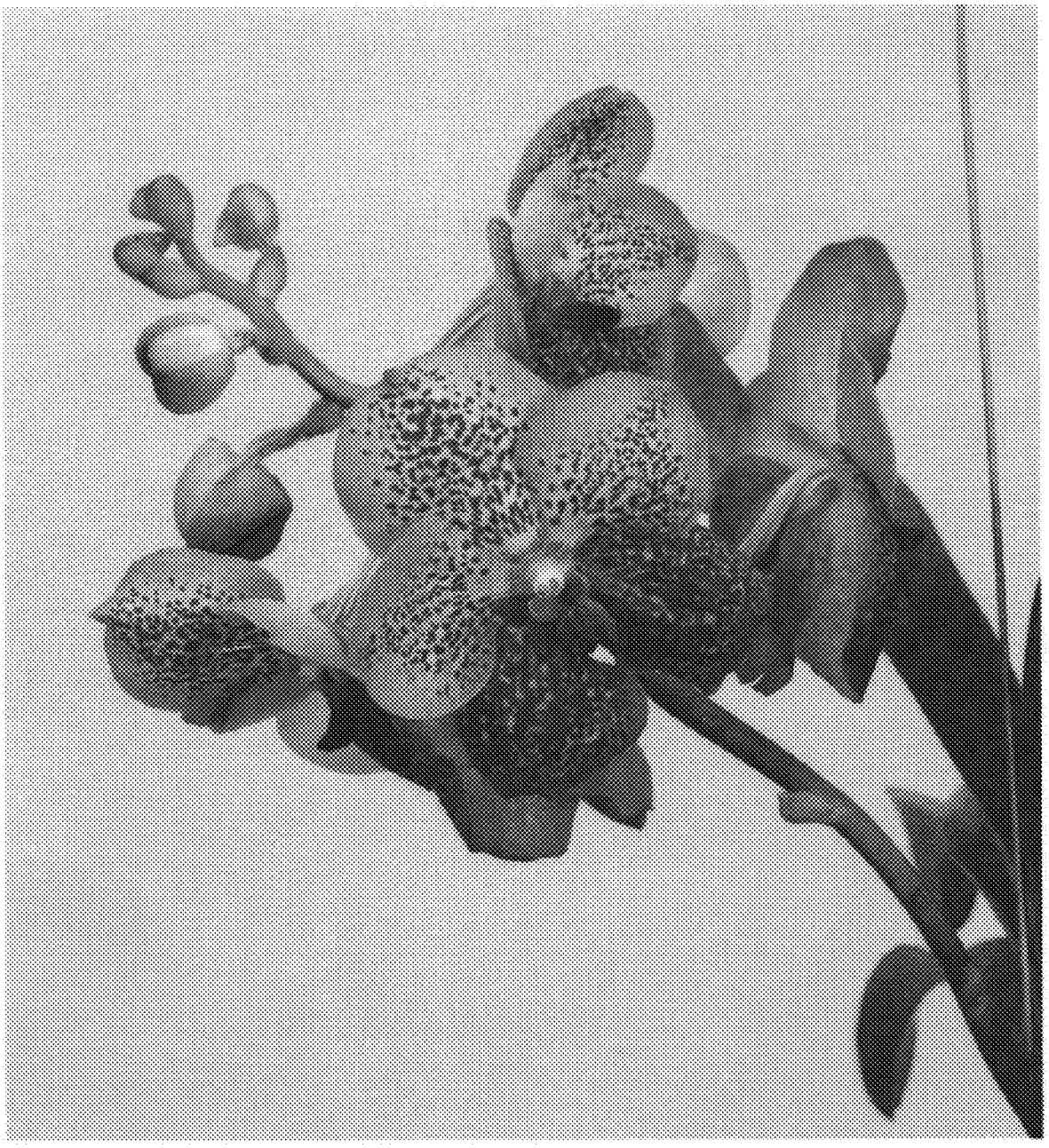
FIG. 3 illustrates, as nearly true as it is reasonably possible to make the same in color photographs of this type, the typical inflorescence of 'SPCDW1809'.
Figure 4:
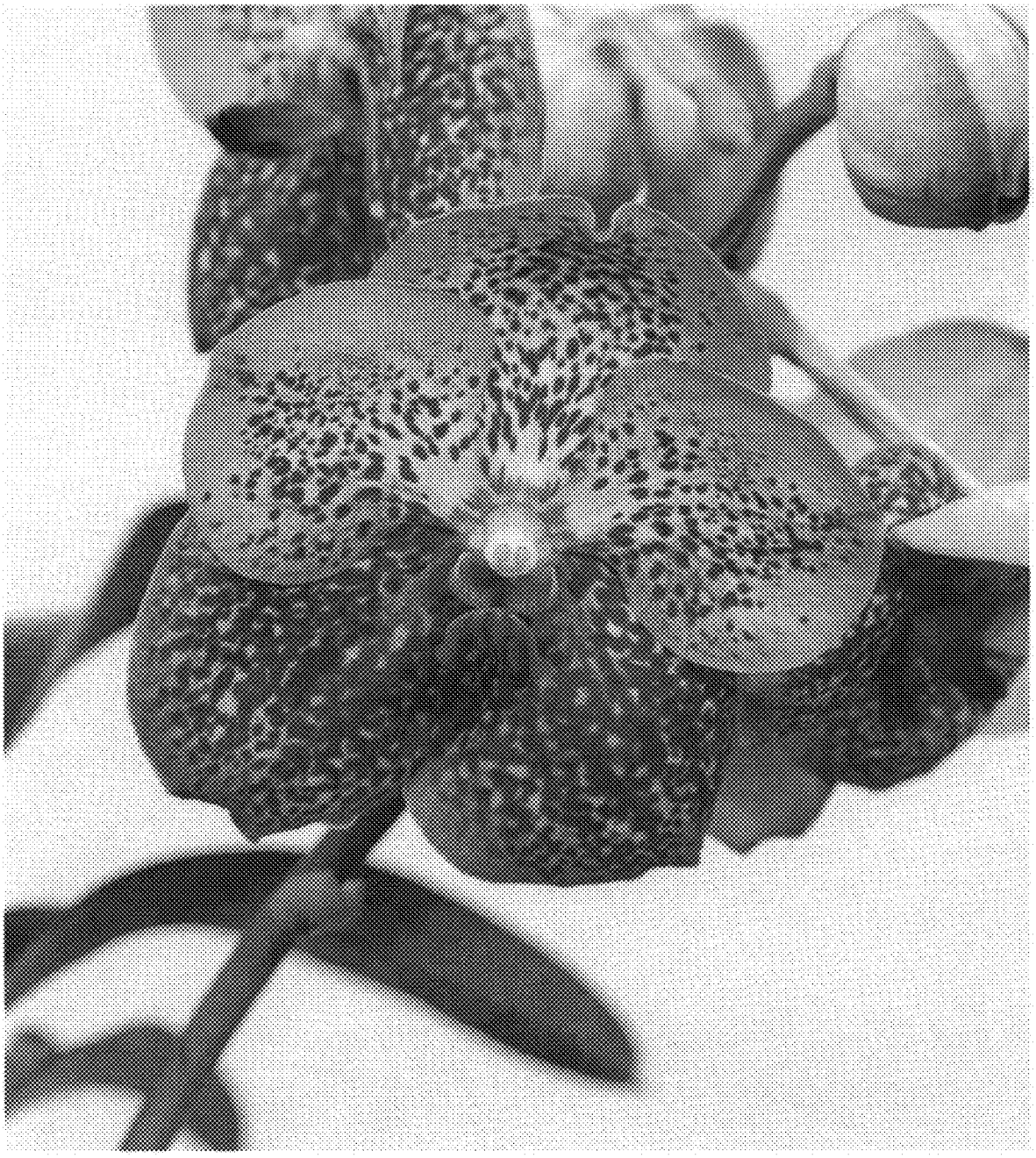
FIG. 4 illustrates, as nearly true as it is reasonably possible to make the same in color photographs of this type, the typical flower of 'SPCDW1809'.

The following observations and measurements made in March of 2019 describe averages from a sample set of six specimens of six year-old 'SPCDW1809' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1809' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'SPCDW1809' and comparisons with the parents and most similar commercial variety of *Vanda* are provided below.

Plant description:

*Growth habit.*—Perennial; monopodial, upright. Single monopodial leafy stem, with flowers carried below to slightly above the leaf plane; inflorescences growing from the leaf axils.

*Average height from base (plant grown in hanging basket, so no soil line present) to foliar plane.*—43.1 cm.

*Average height from base (plant grown in hanging basket, so no soil line present) to top of floral plane.*—46.5 cm.

*Plant spread.*—Average of 53.0 cm.

*Appropriate container size.*—8 cm by 2 cm rectangular hanging basket.

*Growth rate.*—Moderate.

*Plant vigor.*—Moderate.

*Propagation type.*—Meristematic tissue culture propagation using the base of the leaves.

*Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility.*—Plants have not been observed to be susceptible or resistant to pathogens and pests common to *Vanda*.

*Environmental tolerances.*—Adapt to, at least, USDA Zones 11 and 12 and temperatures as high as 40 degrees Celsius; high tolerance to rain; moderate to high tolerance to wind.

Root system:

*General.*—Moderately to densely rooting; with aerial roots only.

*Dimensions, mature roots.*—45.3 cm long with a diameter of 0.7 cm, on average.

*Texture.*—Very fleshy; non-fibrous.

*Color.*—Greyed-green, nearest to RHS 192C; root apex is yellow-green, RHS 146B.

Stem:

*Branching habit.*—Monopodial; no lateral branches present.

*Number of primary (main) stems per plant.*—One.

*Number of secondary (lateral) branches per plant.*—None.

*Aspect.*—Circular, formed by the leaf sheaths.

*Length.*—21.5 cm.

*Diameter.*—1.1 cm.

*Internode length.*—1.1 cm.

*Pubescence.*—Glabrous.

*Luster.*—Matte.

*Attitude, main stem.*—Near vertical.

*Strength.*—Very strong.

*Color, juvenile.*—Yellow-green, nearest to RHS 145D.

*Color, mature.*—Yellow-green, nearest to RHS 145C.

*Color at internodes.*—Yellow-green, nearest to RHS 145C.

Foliage:

*Arrangement.*—Distichous.

*Dimensions.*—30.4 cm long, excluding the sheath, and 3.0 cm wide.

*Shape of blade.*—Ligulate.

*Aspect.*—Moderately to strongly carinate and slightly curled inward.

*Attitude.*—Moderately curled downward.

*Apex.*—Unequal praemorse.

*Base.*—Sheathing.

*Sheath dimensions.*—4.2 cm long and 1.3 cm wide, on average.

*Sheath color.*—Yellow-green, nearest to RHS 145B.

*Margin.*—Entire.

*Pubescence, texture and luster of adaxial surface.*—Glabrous, smooth, and very slightly glossy.

*Pubescence, texture and luster of abaxial surface.*—Glabrous, smooth, and matte.

*Color.*—Juvenile foliage, adaxial surface — Green, nearest to in between RHS 141A and 143A, and darker towards the margins and apex, nearest to RHS 137A. Juvenile foliage, abaxial surface — Nearest to in between green and yellow-green, RHS 143B and 144A, and becoming green towards the margins and apex, nearest to RHS 137B. Mature foliage, adaxial surface — Green, nearest to RHS 137B, and darker towards the margins and apex, nearest to RHS NN137B. Mature foliage, abaxial surface — Green, nearest to a mixture of RHS 143B and 143C, and darker towards the margins and apex, nearest to RHS 137B.

*Venation.*—Pattern — Parallel. Color, adaxial surface — Green, nearest to RHS 137B. Color, abaxial surface — Green, nearest to RHS 143C.

*Petiole.*—No petioles present; leaves sessile.

Inflorescence:

*Inflorescence arrangement.*—Axially placed raceme.

*Natural flowering season.*—Autumn into winter.

*Time to flower.*—Approximately 10 months.

*Flowers per inflorescence.*—Average of 12.

*Flowers per plant.*—7 open flowers and 5 flower buds.

*Inflorescence height.*—Approximately 23.4 cm (measured from base of lowest flower to top of upper flower).

*Inflorescence diameter.*—Approximately 21.6 cm.

*Peduncle.*—Dimensions — Approximately 41.2 cm long and 0.8 cm wide. Attitude — Generally at a 30 degree angle to lateral branch axis. Strength — Moderately strong. Texture and luster — Glabrous and matte. Color — Green, nearest to RHS 143B.

Bud:

*Length.*—Average of 2.1 cm.

*Diameter.*—Average horizontal diameter is 2.4 cm; the vertical diameter is 2.4 cm.

*Shape.*—Broad obovate to near globular, with a deltoid apex which is pointed downward.

*Pubescence, texture and luster.*—Glabrous, smooth and slightly glossy.

*Color.*—A mixture of yellow-green and greyed-orange, nearest to RHS 145C, 151B and N170C, and suffused with greyed-purple towards the apex, nearest to RHS 183B; buds are slightly dotted greyed-purple, nearest to RHS 183D.

Flower:

*Flower type.*—Zygomorphic (orchidaceous), typical shape for the genus *Vanda*.

*Flowering habit.*—Moderately free flowering.

*Shape.*—Zygomorphic, single; consisting of three sepals and three petals, one of which is transformed into a labellum; the two lateral petals strongly overlap the lateral and dorsal sepals; lateral sepals are touching to slightly overlapping one another.

*Attitude.*—Flowers are outward-facing to slightly nodding.

*Vertical height.*—Approximately 11.8 cm.

*Diameter.*—Approximately 11.1 cm.

*Depth.*—Approximately 4.1 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 5.3 cm. Width — Approximately 5.2 cm. Shape — Broad ovate to near orbicular. Apex — Obtuse. Base — Cuneate. Margin — Entire; not undulated. Pubescence, texture and luster of upper surface — Glabrous, velvety and matte. Pubescence, texture and luster of lower surface — Glabrous, velvety and matte. Color when opening, upper surface — Yellow, nearest to a mixture of RHS 2C and 2D, and suffused with orange-red towards the margins and apex, nearest to a mixture of RHS 35C and 35D; base of petal is greyed-red, nearest to RHS 178B; petals are moderately dotted greyed-purple, nearest to a mixture of RHS 187C and 187D. Color when opening, lower surface — Yellow, nearest to RHS 4D, and suffused with orange-red towards the margins and apex, nearest to RHS 35C. Color when fully opened, upper surface — Greyed-red, nearest to RHS 179C, and fading to yellow towards the base, nearest to RHS 10C; base of petals is greyed-orange, nearest to RHS 174B; petals are moderately dotted greyed-purple, nearest to RHS 187B. Color when fully opened, lower surface — Yellow, nearest to RHS 11C, and suffused with a mixture of orange-red and greyed-red towards the margins and apex, nearest to RHS 37A and 180D. Fading, upper surface — Not fading. Fading, lower surface — Not fading. Venation color, fully opened, upper surface — Greyed-red, nearest to RHS 179C, and fading to yellow towards the base, nearest to RHS 10C; heavily dotted greyed-purple, nearest to RHS 187B. Venation color, fully opened, lower surface — Main vein is greyed-orange, nearest to RHS 164C. No other veins are visible.

*Labellum.*—Shape — Three-lobed; the lateral lobes are reniform and involute; the central lobe is broad oblong and moderately revolute. Length — Central lobe — Approximately 2.0 cm. Lateral lobes — Approximately 0.7 cm. Width — Central lobe — Approximately 1.6 cm at the base; 1.0 at the apex. Lateral lobes — Approximately 1.0 cm. Apex — Central lobe — Emarginate. Lateral lobes— Obtuse. Base — Central lobe — Broad cuneate. Lateral lobes — Broad cuneate. Margin — Central lobe — Entire; moderately undulated. Lateral lobes — Entire; not undulated. Texture and luster of upper surface — Central lobe — Glabrous, velvety, and matte; apex is moderately glossy. Lateral lobes — Glabrous, velvety, and matte. Texture and luster of lower surface — Central lobe — Glabrous, velvety, and matte except for the apex which is slightly glossy. Lateral lobes — Glabrous, velvety, and matte. Color when opening, upper surface — Central lobe — Greyed-red, nearest to a mixture of RHS 182A and 182B, and becoming progressively suffused with greyed-purple towards the apex, nearest to RHS N186C. Lateral lobes — Yellow-green, nearest to RHS 153D, and radially striped greyed-orange, nearest to RHS 177D. Color when opening, lower surface — Central lobe — Greyed-red, nearest to RHS 181A, and lightly suffused with greyed-brown, nearest to RHS 199D; fading to greyed-yellow towards the base, nearest to RHS 161A; becoming progressively suffused with greyed-purple towards the apex, nearest to RHS N186C. Lateral lobes — Yellow-green, nearest to RHS 154B, and radially striped greyed-orange, nearest to RHS 177D. Color when fully opened, upper surface — Central lobe — Greyed-red, nearest to RHS 182A, and becoming progressively suffused with greyed-purple towards the apex, nearest to RHS N186C. Lateral lobes — Yellow-green, nearest to RHS 153D, and radially striped greyed-orange, nearest to RHS 177D. Color when fully opened, lower surface — Central lobe — Greyed-red, nearest to RHS 181A, and lightly suffused with greyed-brown, nearest to RHS 199D; fading to greyed-yellow towards the base, nearest to RHS 161A; becoming progressively suffused with greyed-purple towards the apex, nearest to RHS N186C. Lateral lobes — Yellow-green, nearest to RHS 154B, and radially striped greyed-orange, nearest to RHS 177D. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities.*—Dimensions — 1.8 cm long and 0.8 cm wide, on average. Color — Greyed-purple, nearest to RHS N186C, and fading to yellow towards the base, nearest to RHS 11B.

*Spurs.*—Quantity — Average of 1. Length — Approximately 0.9 cm. Diameter — Approximately 0.4 cm. Vertical height — Approximately 0.8 cm, at the base. Shape — Short triangular; flattened. Apex — Bluntly acute. Base — Broad cuneate. Pubescence, texture and luster — Glabrous, smooth, and matte. Color — Yellow-green, nearest to RHS 154D, and radially striped greyed-orange, nearest to RHS 177D.

*Sepals.*—Quantity — Average of 3 unfused sepals. Arrangement — One dorsal sepal and two lateral sepals. Length — Dorsal sepal — Approximately 6.1 cm. Lateral sepals — Approximately 6.1 cm. Width — Dorsal sepal — Approximately 6.1 cm. Lateral sepals — Approximately 7.0 cm. Shape — Dorsal sepal — Near orbicular. Lateral sepals — Reniform. Apex — Dorsal sepal — Obtuse. Lateral sepals — Obtuse. Base — Dorsal sepal — Cuneate. Lateral sepals — Cuneate. Margin — Dorsal sepal — Entire; very lightly undulated. Lateral sepals — Entire; moderately undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Yellow, nearest to RHS 2D, and suffused with greyed-red towards the margins and apex, nearest to RHS 179D; base of petal is greyed-red, nearest to RHS 178B; sepal is moderately dotted greyed-purple, nearest to RHS 187B. Lateral sepals — Nearest to a mixture of yellow and yellow-green, RHS 4B and 154C, and suffused with greyed-orange towards the margins and apex, nearest to a mixture of RHS 176C and 176D; sepals are heavily dotted greyed-purple, nearest to a mixture of RHS 187C and 187D. Color when opening, lower surface — Dorsal sepal — Yellow, nearest to RHS 4D, and suffused with red centrally and also towards the margins and apex, nearest to RHS 51C. Lateral sepals — Nearest to a mixture of yellow and yellow-green, RHS 4B and 154C, and suffused with greyed-purple towards the margins and apex, nearest to a mixture of RHS 183C and 183D. Color when fully opened, upper surface — Dorsal sepal — Yellow, nearest to RHS 3D, and suffused with greyed-red towards the margins and apex, nearest to RHS 179C; base of petal is greyed-red, nearest to RHS 178B; sepal is moderately dotted greyed-purple, nearest to RHS 187B. Lateral sepals — Yellow, nearest to a mixture of RHS 3B and 3C, and suffused with greyed-red towards the margins and apex, nearest to RHS 182B; sepals are heavily dotted and blotched greyed-purple, nearest to a mixture of RHS 183A and 187A. Color when fully opened, lower surface — Dorsal sepal — Yellow, nearest to RHS 3D, and suffused with red towards the margins and apex, nearest to a mixture of RHS 48B and 48C. Lateral sepals — Nearest to a mixture of yellow and yellow-green, RHS 4B and 154C, and suffused with greyed-purple towards the margins and apex, nearest to RHS 183C. Fading, upper surface — Not fading. Fading, lower surface — Not fading. Venation color, fully opened, upper surface — Dorsal sepal — Yellow, nearest to RHS 3D, and suffused with greyed-red towards the margins and apex, nearest to RHS 179C; heavily dotted greyed-purple, nearest to RHS 187B. Lateral sepals — Yellow, nearest to a mixture of RHS 3B and 3C, and suffused with greyed-red towards the margins and apex, nearest to RHS 182B; sepals are heavily dotted and blotched greyed-purple, nearest to a mixture of RHS 183A and 187A. Venation color, fully opened, lower surface — Dorsal sepal — Main vein is greyed-orange, nearest to RHS 173C. No other veins are visible. Lateral sepals — Main vein is greyed-orange, nearest to RHS 173C. No other veins are visible.

*Pedicels.*—Length — Approximately 6.7 cm. Diameter — Approximately 0.65 cm. Attitude — Approximately 90 degree angle to peduncle axis. Strength — Moderately strong. Texture — Glabrous, axially angled with 5 "ribs", axially twisted (due to resupination). Luster — Glossy. Color — Red-purple, nearest to RHS 59D, and fading to greyed-green towards the proximal end, nearest to RHS 195B; ribs are white, nearest to RHS N155C.

*Bract.*—Quantity — One bract present at the base of each pedicel. Shape — Reniform; folded around the base of each pedicel. Dimensions — Average of 1.9 cm long and 2.2 cm wide. Apex — Broad obtuse. Base — Broad cuneate. Margins — Entire: Color, inner surface — Yellow-green, nearest to a mixture of RHS 144B and 144C, and margined yellow-green, RHS 151D. Color, outer surface — Yellow-green, nearest to a mixture of RHS 144B and 144C, and margined yellow-green, RHS 151D.

Reproductive organs:

*Column.*—Length — Approximately 0.6 cm. Diameter — Approximately 0.8 cm. Color — Yellow, nearest to RHS 4C; base is suffused with red, nearest to RHS 51C.

*Ovary.*—Position — Inferior. Diameter — Approximately 0.2 cm. Color — Yellow-green, nearest to RHS 150D.

*Pollinia color.*—Yellow-orange, nearest to RHS 14A.

Seed and fruit: No fruit and seed production has been detected to date.

Comparison with the parent plants: Plants of the new cultivar 'SPCDW1809' differ from the *Vanda* seed parent, 'GM' (not patented), by the characteristics described in Table 1.

TABLE 1

| Characteristic | 'SPCDW1809' | 'GM' |
|---|---|---|
| Vigor; rate of growth. | Faster growing than 'GM'. | Slower growing than 'SCDW1809'. |
| Bloom habit. | Substantially more freely flowering. | Less freely flowering. |
| Lastingness of flowers. | Longer lasting than 'GM'. | Flowers are shorter lived than those of 'SPCDW1809'. |
| Flower size. | Substantially larger than 'GM'. | Smaller than 'SPCDW1809'. |
| General coloration of the petals and sepals when fully opened. | Light yellow, suffused with greyed-red; dotted and blotched greyed-purple. | Yellow; blotched and dotted red. |

Plants of the new cultivar 'SPCDW1809' differ from the *Vanda* pollen parent, *Vanda* 'M81R1' (not patented), by the characteristics described in Table 2.

TABLE 2

| Characteristic | 'SPCDW1809' | 'M81R1' |
|---|---|---|
| Vigor; rate of growth. | Substantially slower-growing than 'M81R1'. | Faster growing than 'SCDW1809'. |
| Bloom habit. | More freely flowering. | Less freely flowering. |

TABLE 2-continued

| Characteristic | 'SPCDW1809' | 'M81R1' |
|---|---|---|
| Inflorescence height. | Shorter than 'M81R1'. | Longer than 'SPCDW1809'. |
| Flower size. | Larger than 'M81R1'. | Smaller than 'SPCDW1809'. |
| General coloration of the petals and sepals when fully opened. | Light yellow, suffused with greyed-red; dotted and blotched greyed-purple. | Purple; dotted and blotched red. |

Comparison with the most similar *vanda* cultivar known to the inventor: Plants of the new cultivar 'SPCDW1809' are similar to the cultivar, *Vanda* 'SPCDW1610' (Community Plant Variety Rights grant number 50566). A comparison of 'SPCDW1809' with *Vanda* 'SPCDW1610' is described in Table 3.

TABLE 3

| Characteristic | 'SPCDW1809' | 'SPCDW1610' |
|---|---|---|
| Lateral sepal position, relative to the dorsal sepal. | More overlapping. | Less overlapping. |
| General coloration of the petals and sepals when fully opened. | Light yellow, suffused with greyed-red; dotted and blotched greyed-purple. | Red; blotched and dotted orange. |

That which is claimed is:

1. A new and distinct variety of *Vanda* plant named 'SPCDW1809', substantially as described and illustrated herein.

* * * * *